US006924267B2

(12) United States Patent
Daemen et al.

(10) Patent No.: US 6,924,267 B2
(45) Date of Patent: Aug. 2, 2005

(54) METHODS AND ACTIVE SUBSTANCES FOR PROTECTING ORGANS

(75) Inventors: Marc A. R. C. Daemen, Sittard (NL); Vincent H. Heemskerk, Maastricht (NL); Cornelis van't Veer, Meerssen (NL); Geertrui Denecker, Veldegem (BE); Tim G. A. M. Wolfs, Maastricht (NL); Peter Vandenabeele, St-Amandsberg (BE); Wim A. Buurman, Eijsden (NL); Jaakko Parkkinen, Espoo (FI)

(73) Assignee: Suomen Punainen Risti Veripalvelu, Helsinki (FI)

( * ) Notice: Subject to any disclaimer, the term of this patent is extended or adjusted under 35 U.S.C. 154(b) by 309 days.

(21) Appl. No.: 09/956,606

(22) Filed: Sep. 18, 2001

(65) Prior Publication Data

US 2003/0053998 A1 Mar. 20, 2003

(51) Int. Cl.$^7$ .......................... A61K 38/16; A01N 1/00; C07K 14/00
(52) U.S. Cl. ................... 514/8; 514/2; 514/6; 435/1.1; 435/1.2; 530/380; 530/392; 530/395; 530/416; 530/417; 530/422; 530/830; 530/831
(58) Field of Search ................ 514/8, 2, 6; 435/1.1, 435/1.2; 530/380, 392, 395, 416, 417, 422, 830, 831

(56) References Cited

U.S. PATENT DOCUMENTS

2003/0069174 A1    4/2003  Pichler et al.

FOREIGN PATENT DOCUMENTS

WO        WO 97/32893     *  9/1997

OTHER PUBLICATIONS

Daemen et al., Circulation, vol. 102, No. 12, pp. 142–1426, Sep. 19, 2000.*
Collard, Charles D et al., "Pathophysiology, clinical manifestations . . . ", Anesthesiology, vol. 94, No. 6, Jun. 2001, pp. 1133–1138.
Squifflet, J. P. et al., "Safe preservation of human renal . . . ", Transplantation Proceedings, vol. XIII, No. 1, Mar. 1981, pp. 693–696.
Maxwell, Simon R.J. et al., "Reperfusion injury: a review . . . ", International Journal of Cardiology, (1997) vol. 59, pp. 95–117.
Daemen, Marc A. R. C. et. al., "Inhibition of apoptosis induced by . . . ", The Journal of Clinical Investigation, Spetember 1999, vol. 104, No. 5, pp. 541–549.
Molle, Wim Van et al., "$\alpha_1$–Acid glycoprotein and $\alpha_1$–Antitrypsin inhibit . . . ", The Journal Immunology, (Oct 1, 1997), 159(7), pp. 3555–3564.
Williams, Julian P. et al., "$\alpha_1$–Acid glycoprotein reduces local . . . ", American Journal of Physiology, Nov 1997, 273 (5 Pt 1), p. G1031–5.
Huang, Jianmin et al., "Expression and purification of functional . . . ", Biotechnol. Prog., (2001), 17, pp. 126–133.
Burnouf–Radosevich, M. et al., "Nanofiltration, a new specific virus . . . ", Vox Sang, (1994) 67, pp. 132–138.
Hao, Yu–Lee et al., "Development of large–scale fractionaiton methods IV . . . "Biochim Biophys Acta., Sep 21 1973, 322(1), pp. 99–108.
Daemen, Marc A.R.C. et al., "Functional protein by acute . . . ", Circulation, Sep 19 2000, 102(12), p. 1420–6.
De Graaf, Truus W., "Inflammation–induced expression of sialyl . . . ", J Exp Med., Mar 1, 1993, 177(3), pp. 657–66.
Pichler, et al., Preclinical investigatios of $\alpha_1$_acid glycoportein (orosomucoid), Wien Klin Wochenschr (the middle european journal of medicine) (1999) 111/5: 192–198.

* cited by examiner

Primary Examiner—Jon Weber
Assistant Examiner—Abdel A. Mohamed
(74) Attorney, Agent, or Firm—Birch, Stewart, Kolasch & Birch, LLP (57) ABSTRACT

The present invention comprises a method of protecting organs or tissue susceptible to reperfusion-induced dysfunction after ischemia. The method comprises parenterally administering to a patient a therapeutical composition containing natural alpha-1 acid glycoprotein, natural alpha-1 antitrypsin or a mixture thereof. Alternatively, organ or tissue transplants can be contacted with natural alpha-1 acid glycoprotein, natural alpha-antitrypsin or mixtures by perfusing or flushing them with a solution containing natural alpha-1 acid glycoprotein, natural alpha-1 antitrypsin or mixtures thereof in a concentration of 0.1 to 5 g/l.

23 Claims, 4 Drawing Sheets

METHODS AND ACTIVE SUBSTANCES FOR PROTECTING ORGANS

BACKGROUND OF THE INVENTION

1. Field of Invention

The present invention relates to protection of organs, tissues and organ functions during reperfusion of ischemic organs. In particular, the invention relates to prevention of functional impairment of organs caused by ischemia-reperfusion during organ transplantation, surgical operations in general, thrombolytic therapy, after major blood loss and other causes of shock and hypoperfusion of organs.

2. Description of Related Art

Prolonged ischemia followed by reperfusion induces apoptosis and inflammation leading to tissue damage and organ dysfunction, which is called ischemia-reperfusion (I/R) injury or reperfusion injury. I/R injury takes place in various clinical conditions characterized by temporary decrease or complete stop of blood flow to one or several organs (ischemia) followed by restoration of blood flow (reperfusion) (for review, see Collard, C. D. and Gelman, S., Anesthesiology 94:1133–1138, 2001)

Ischemia-reperfusion injury accompanying organ transplantations leads to dysfunction of the transplanted organ. When removed from the donor, organ transplants are perfused with cold preservation solution and subsequently either stored cold or perused with cold preservation solution. This leads to cold ischemia in the organ transplant. After transplantation to the recipient and restoration of blood flow, different extent of I/R injury develops in the organ transplant. In kidney transplantation, I/R injury and concomitant renal dysfunction leads to prolonged dependence on hemodialysis, whereas in heart liver and lung transplantations immediate proper functioning of the graft is even more important and graft dysfunction may lead to death of the patient. The continuously increasing demand of donor organs necessitates the transplantation of organs from marginal donors with impaired blood flow, including so called non-heart beating donors, whose organs are always subjected to prolonged ischemia. This further contributes to I/R injury after transplantation.

Several preservation solutions aiming at minimizing tissue damage in the organ transplants during hypothermal storage have been described. Belzer UW solution disclosed in U.S. Pat. Nos. 4,798,824 and 4,879,283 has proved useful for all organ transplants, both for in situ organ perfusion and cooling in the donor and for cold storage after the organ is harvested. While the Belzer UW solution and some other preservation solutions, such as the Euro-Collins solution (Squifflet J. P. et al., Transplant. Proc. 13:693–696, 1981), have been effective in extending the cold preservation time of organs intended for transplantation, tissue injury during cold storage and particularly during reperfusion still occurs. Therefore, reduction in I/R injury and concomitant dysfunction of organ transplants is desirable. Other preservation solutions for organ perfusion and storage are disclosed in U.S. Pat. Nos. 4,415,556, 5,145,771, 5,693,462, 6,045,990 and 6,110,504, but none of them has addressed the protection of organ transplants against I/R injury.

Another clinical condition associated with I/R injury is impairment of blood supply to a local anatomical area caused by occlusion of the blood vessel by a blood clot (thrombosis). Thrombosis of coronary and brain arteries is a leading cause of death. With thrombolytic (fibrinolytic) therapy the blood clot can be dissolved and blood flow restored, thereby preventing necrosis of the tissues. However, fibrinolytic therapy may be associated with I/R injury and concomitant organ dysfunction with potentially serious clinical complications. Other revascularisation procedures, such as percutaneous transluminal angioplasty and coronary artery bypass surgery may also lead to I/R injury (Maxwell S. R. and Lip G. Y., Int. 1. Cardiol. 58:95–117, 1997).

A further clinical condition associated with temporarily decreased blood flow to tissues and organs comprises surgical operations, such as cardiac surgery with or without cardiopulmonary bypass and angioplastic surgery. For example, cardiac and aortic surgery may result in temporary impairment of blood flow to the kidneys, which results to I/R injury and renal dysfunction.

Hypoperfusion of organs takes also place in various forms of shock, such as caused by excessive bleeding. Upon restoration of adequate blood flow, e.g. by restoring the circulating blood volume, I/R injury may take place (Collard and Gelman, 2001).

Currently, there are no effective ways in clinical practise to prevent I/R injury other than restricting the ischemia period to as short as possible (Collard and Gelman 2001). As evident from the prior art, prevention of I/R injuries would be of utmost clinical importance in the prevention of dysfunction of critical organs in various clinical conditions. Therefore, the present invention aims at providing therapeutic means to prevent I/R injury and consequent organ dysfunction.

SUMMARY OF THE INVENTION

It is an object of the present invention to provide a method of preventing reperfusion-induced organ dysfunction in different clinical conditions associated with ischemia.

It is a second object of the present invention to provide a method of preventing I/R injury associated with organ transplantations, surgical operations in general, thrombolytic therapy and revascularisation procedures of any type of infarction, and treatment of bleeding shock and other forms of shock.

It is a third object of the invention to provide a novel preservation fluid which, when contacted with the organ or tissue which is to be implanted into a recipient patient, is capable of preventing organ and tissue transplants.

It is a fourth object of the present invention to provide a novel pharmaceutical composition which, when administered to the recipient, prevents I/R injury of organ transplants.

It is a fifth object to provide a method and a novel pharmaceutical composition for preventing I/R injury of a patient undergoing major surgery, such as cardiac and angioplastic surgery.

It is a sixth object to provide a method and a pharmaceutical composition for preventing I/R injury of patients undergoing thrombolytic therapy or revascularisation procedures or treatment of bleeding shock or other forms of shock.

The invention is based on the surprising finding that two plasma proteins, viz. alpha-1 acid glycoprotein (AGP) and alpha-1 antitrypsin (AAT), effectively prevent reperfusion-induced organ dysfunction after ischemia. When AGP or AAT or mixtures thereof are administered to an animal, in which the blood flow to an organ is temporarily closed to induce ischemia and subsequently the blood flow is restored, the I/R injury which otherwise develops to the organ is effectively prevented. In particular, the AGP or AAT proteins used are plasma-based, i.e. isolated and purified from blood plasma of mammals, in particular humans, or they comprise transgenic or recombinant alpha-1 acid glycoprotein or alpha-1 antitrypsin having an amino acid sequence identical or essentially identical with that of the corresponding human glycoprotein. As will be discussed in more detail below, the AGP and AAT used can be purified from human plasma or they can be produced by recombinant DNA technology as transgenic proteins in animals or plants or in cell culture. The glycosylation pattern of the AGP and AAT is preferably similar to that of plasma-AGP or plasma-AAT, respectively, According to the present invention the novel method of protecting organs or tissue susceptible to reperfusion-induced dysfunction after ischemia, comprises contacting the organs or tissue with an increased concentration of natural alpha-1 acid glycoprotein, natural alpha-1 antitrypsin or a mixture thereof during the ischemia period or immediately upon reperfusion, preferably no later than at the beginning of the reperfusion period to prevent apoptosis. The "contacting" can take place both in vivo and in vitro. Thus, AGP and/or AAT can be parenterally administered to a patient, who has organs or tissue susceptible to a condition of reperfusion-induced dysfunction after ischemia. On the other hand, it is also possible to carry out the invention by perfusing organ or tissue transplants with a preservation fluid and store the organ or tissue transplants for a sufficient time prior to the implantation of said organ or tissue in a patient requiring such implantation, whereby the preservation solution contains natural alpha-1 acid glycoprotein, natural alpha-1 antitypsin or mixtures thereof in an effective concentration. AGP, AAT or mixtures thereof can be also added to a rinse solution used for flushing the organ or tissue transplant before transplantation into the recipient. Other embodiments of the invention will be discussed in more detail below.

The present invention provides several advantages. Being physiological plasma proteins, human AGP and AAT are not toxic or foreign proteins to human subjects. The administered amounts of AAT and AGP that are effective in the prevention of I/R injuries result in plasma concentrations which are similar to those occurring in plasma during inflammatory conditions. The plasma levels of AGP and AAT increase considerably in inflammatory conditions, which is called acute phase response. Whereas the rise in the level of endogenous AGP and AAT during acute phase response takes place after a lack period and is too late to prevent the tissue injury that has already taken place, the present invention takes advantage of the possibility to increase rapidly AGP and/or AAT level in circulation and tissues by administrating purified exogenous AGP and/or AAT before tissue injury develops. Thus, it is a preferred embodiment of invention to increase the plasma concentration of AGP or AAT or mixtures thereof to a level corresponding to that typical for the acute phase response for a patient susceptible to a condition of inflammation.

According to the present invention it is possible to protect organ transplants by adding AGP and/or AAT to an artificial preservation fluid, which is used for perfusion of the organ transplant before cold storage or for continuous perfusion during cold storage.

Human AGP is readily available in large volumes as a side product of present blood fractionation, and the present invention provides an important way of utilizing this source of the protein which to date has had limited commercial value.

Next, the present invention will be examined more closely with the aid of the following detailed description and with reference to a number of working examples.

DETAILED DESCRIPTION OF THE INVENTION

Generally, the present invention comprises a method of protecting organs or tissue susceptible to reperfusion-induced dysfunction after ischemia, wherein said organs or tissue are contacted with an increased concentration of natural AGP, natural AAT or a mixture thereof. For the purpose of the present invention, the term "increased concentration" stands for concentrations of said glycoproteins which are higher than those which the organ or tissue would otherwise encounter without the implementation of the present invention. Thus, the organs or tissue can be contacted with increased concentrations of AGP, AAT or mixtures thereof by parenterally administering about 20 to 500 mg/kg/day of said glycoproteins to a patient who has organs or tissue susceptible to a condition of reperfusion-induced dysfunction after ischemia, so as to raise the concentration of the proteins in the plasma. Usually, the plasma concentration is increased by at least 50%, preferably by at least 100%, compared to the plasma concentration prevailing without the active intervention during the implementation of the method of therapy. Typically, the concentration of AGP, AAT or a mixture thereof in the plasma of a patient is 2- to 6-times higher than before the intervention. For instance, the plasma concentrations of said proteins can be raised to a level essentially corresponding to that occurring in plasma during inflammatory conditions. Depending on the patient and his or her condition before the administration of AGP or AAT, that concentration can vary in the range of about 0.2 to 5 g/l.

The present invention shows that AGP and AAT effectively prevent I/R injury when administered parenterally. As evident from Examples 1 to 4, AGP and AAT effectively prevent reperfusion-induced apoptosis, inflammation and functional impairment in an ischemic organ. It is known from prior studies (Daemen M. A. et al., J. Clin. Invest.

104:541–9, 1999) that acute primary apoptosis during early reperfusion is crucial to the initiation of reperfusion-induced inflammation and development of I/R injury. According to the present invention, AGP and AAT administered at time of reperfusion effectively prevent acute primary apoptosis, as indicated by assessment of apoptosis markers 2 hours after reperfusion (Example 1).

AGP and AAT administered at the time of reperfusion also effectively prevent inflammation and apoptosis 24 hours after reperfusion (Examples 1 and 2). When AGP and AAT were administered 2 hours after the initiation of reperfusion, they still prevented inflammation and late apoptosis but clearly to a lesser extent This suggests that AGP and AAT may have direct anti-inflammatory effects and can also prevent TNF-α-dependent late apoptosis. However, according to the present invention these effects are less important in the prevention of I/R injury. As evident from Example 3, AGP and AAT administered at time of reperfusion effectively protected against reperfusion-induced organ dysfunction whereas their administration 2 hours after the initiation of reperfusion failed to protect against organ dysfunction. This emphasizes the importance of early administration of AGP and AAT and prevention of acute primary apoptosis during reperfusion.

As far as the present invention is concerned, AGP and/or AAT should be administered before, at or not later than 60 minutes after the initiation of reperfusion. In particular it is preferred to administer AGP and/or AAT no later than 30 minutes after the initiation of reperfusion.

AGP has previously been shown to protect against TNF-α-induced liver apoptosis in galactosamine-pretreated and actinomycin D-pretreated mice, whereas AAT conferred protection only in the galactosamine model (Van Molle W. et al., J. Immunol. 159:35555–35564, 1997). By contrast, according to the present invention, AGP and AAT effectively protect against the early primary apoptosis during reperfusion, which is critical to the initiation of reperfusion-induced inflammation. Importantly, early primary apoptosis is not dependent on TNF-α. Further, according to the present invention prevention of the early apoptosis is crucial for protection against reperfusion-induced organ dysfunction after ischemia. Additionally, the prior art is silent of the potential therapeutic use of AGP or AAT in the prevention of I/R injury.

In another prior study, a recombinantly engineered form of AGP enriched with sialyl Lewis$^x$ (sLe$^x$) carbohydrate structures (sAGP) was shown to reduce local and remote injuries after intestinal ischemia in a rat model (Williams J. P. et al., Am. J. Physiol. 273:G1031–G1035, 1997). Although the article does not disclose the actual amount of sLe$^x$ in the sAGP, the concentration was "increased" which indicates that the recombinantly engineered sAGP protein did not correspond to plasma-AGP. sAGP reduced remote lung injury by 62% and complement-dependent intestinal injury by 28%. According to the reference, this protection was attributed to sLe$^x$-mediated inhibition of neutrophil and complement-mediated injuries. As discussed above, in the present invention, the AGP corresponds to natural plasma-AGP and therefore contains very small amounts of sLe$^x$, if any. Further, the present invention has shown that the protective effect of AGP is not dependent on sLe$^x$ determinants (Example 4). Thus, it is possible to obtain valuable and surprising results even with AGP which is essentially free of sLe$^x$.

In another important embodiment of the invention, to protect organ transplants, AGP and AAT can be added to the preservation fluid used for in situ organ perfusion and cooling in the donor and for cold storage or perfusion after the organ is harvested. The organ or tissue transplants can be perfused or flushed with a solution containing AGP, AAT or mixtures thereof in a concentration of 0.1 to 5 g/l. Typically, the organs or tissue are perfused with a solution containing, in addition to AGP, AAT or a mixture thereof, also at least one component selected from the group consisting of electrolytes and cell-protecting agents.

According to the present invention, human or similar natural AGP preparation is used. The preparations according to the examples below, which proved to be effective in the prevention of I/R injury, have been purified from the plasma of healthy blood donors and contain only little sLe$^x$ determinants (about 10% of the protein). Further, we have found that removal of AGP molecules with possible sLe$^x$ determinants by affinity chromatography does not influence the protective effect of normal human AGP. This indicates that human AGP does not need to be reconstructed to contain increased levels of sLe$^x$ determinants in order to be effective in the prevention of I/R injury. On the contrary, according to the present invention, the AGP glycoproteins used are "natural" proteins in the sense that they contain no sLe$^x$ determinants or possibly sLe$^x$ determinants up to a level corresponding to that present in plasma AGP (i.e. a maximum of about 10% of the protein).

Furthermore, according to the present invention the effect of AGP and AAT is rapid and apoptosis is inhibited before any neutrophil infiltration is observed, and an effect on leukocytes less important in protection against reperfusion-induced organ dysfunction after ischemia.

In summary, when used for treating patients, AGP and AAT are, according to the present invention, administered by parenteral route, preferably intravenously. It is preferred to administer them rapidly after initiation of reperfusion, most preferably at the time of reperfusion of ischemic organs. They can be given intravenously to the recipient before or after transplantation, preferably no later that during the transplantation.

Effective concentrations of AGP and AAT in plasma are identical or below the levels occurring in human subjects during acute phase response. This corresponds to plasma levels up to 5 g/l. Intravascular doses of AGP and AAT that are effective in the treatment of humans are in the range of 20–500 mg/kg/day.

Turning now to the use of AGP and AAT in preservation or rinse solutions it can be reiterated that by adding AGP and/or AAT to the preservation solution used for organ perfusion and cooling in the donor and for cold storage or perfusion after the organ is harvested, I/R injury in the organ transplant can be prevented and functional recovery after transplantation promoted. AGP and AAT may be added to different types of preservation solutions, which typically contain electrolytes (such as $Na^+$, $K^+$, $Mg^{++}$, $Cl^-$, $SO_4^{2-}$, $HPO_4^{2-}$, $Ca^{2+}$ and $HCO_3^-$) and may contain various other agents protecting the cells during cold storage. For example, AGP and/or AAT can be added to the UW Belzer solution (VIASPAN® Cold Storage Solution, DuPont Pharmaceuticals Company), which contains 50 g/l hydroxyethyl starch, 35.83 g/l lactobionic acid, 3.4 g/l potassium phosphate monobasic, 1.23 g/l magnesium sulfate heptahydrate, 17.83 g/l raffinose pentahydrate, 1.34 g/l adenosine, 0.136 g/l allopurinol, 0.922 g/l glutathionine, 5.61 g/l potassium hydroxide and sodium hydroxide for adjustment of pH to pH 7.4. Another example of a suitable preservation solution is the Euro-Collins solution, which contains 2.05 g/l monopotassium phosphate, 7.4 g/l dipotassium phosphate, 1.12 g/l potassium chloride, 0.84 g/l sodium bicarbonate and 35 g/l glucose. These intracellular type preservation solutions are rinsed away from the donor organ before completion of transplantation into the recipient by using a physiological infusion solution, such as Ringer's solution, and AGP and/or AAT can be also added to a rinse solution. Further, AGP and/or AAT can be added to extracellular type preservation solutions which need to be flushed away, such as PEFADEX (Vitrolife, Sweden), which contains 50 g/l dextran, 8 g/l sodium chloride, 400 mg/l potassium chloride, 98 mg/l magnesium sulfate, 46 mg/l disodium phosphate, 63 mg/l potassium phosphate and 910 mg/l glucose.

The novel preservation and rinsing solutions according to the present invention may have a composition essentially corresponding to any of the three commercial solutions described above. However, the actual concentrations of the conventional components may vary somewhat, typically within a range of about ±50%, preferably about ±30%, of the mean values given above. Thus, to give an example, in a novel preservation solution having a basic composition similar to the Belzer solution mentioned above, the concentration of hydroxyethyl starch may vary in the range of about 25 to 75 g/l.

According to a preferred embodiment, to ensure maximum activity, AGP and AAT are added to a ready-made preservation or rinse solution just before use. Alternatively, a suitable preservation solution containing AGP and/or AAT may be prepared beforehand.

By administrating AGP and/or AAT to a recipient of an organ transplant at time of transplantation, development of I/R injury in the organ transplant can be prevented. As a result of this, the function of the organ transplant is more rapidly recovered, which is a prerequisite for the success of the organ transplantation. In kidney transplantions, the prevention of renal dysfunction after transplantation decreases dependence of the patient on hemodialysis. In liver, heart and lung transplantations, the early proper function of the organ transplant is critical and prevention of graft dysfunction should decrease mortality of the patients. By adding AGP and/or AAT to the artificial preservation solution used for organ perfusion and cooling and for cold storage, I/R injury in the organ transplant can be also prevented and functional recovery after transplantation promoted.

By administrating AGP and/or AAT to patients undergoing cardiac or angioplastic surgery, development of I/R injury during operation can be prevented. This decreases the need of postoperative critical care. Correspondingly, by administering AGP and/or AAT to patients undergoing thrombolytic therapy, development of I/R injury during reperfusion of the occluded vessel can be prevented and organ dysfunction can be avoided. In thrombolytic therapy of myocardial infarction this may prevent cardiac arrythmias and cardiac insufficiency. In thrombolytic therapy of brain infarction, this may decrease neurological symptoms and palsies. By administrating AGP and/or AAT to patients suffering from bleeding shock or other forms of shock, development of I/R injury during restoration of adequate circulation can be prevented and functional recovery of critical organs promoted.

According to an embodiment of the present invention, AGP and AAT and mixtures thereof are used in methods for preparing pharmaceutical compositions intended for use in any of the therapeutic methods of treatment described above.

According to the present invention, the AGP and AAT used comprise glycoproteins having amino acid sequences identical or essentially identical with those of human AGP and AAT, respectively. "Essentially identical" refers here to polymorphic sequence variants of AGP and AAT occurring in healthy human subjects. AGP and AAT can be purified from human plasma or they can be produced by recombinant DNA technology as transgenic proteins in animals or plants (cf. for example U.S. Pat. No. 6,194,553, the contents of which is herewith incorporated by reference) or in cell cultures using bacterial, animal, plant or yeast cells (Huang J. et al., Biotechnol. Prog. 17:126–133, 2001). According to the present invention, the therapeutic efficacy is not dependent on specific carbohydrate structures of AGP or AAT, such the sLex determinant. Recombinant AGP and AAT do not need to have an identical glycosylation pattern with the corresponding protein purified from human plasma.

Preferably, the AGP and AAT used should carry a mammalian-type glycosylation pattern.

Purification of AGP can be accomplished from Fraction V supernatant, which is a by-product when albumin is purified from human plasma by the Cohn fractionation method. Being an exceptionally acid protein with a pI of about 2.7, AGP can be effectively purified from other contaminating proteins by ion exchange chromatography. AGP can be bound to an anion exchange resin under conditions in which impurities are washed away, and pure AGP can be eluted from the resin. The functional group of the anion exchange resin can be diethylaminoethyl (DEAE), diethyl(2-hydroxyprolyl)-aminoethyl (QAE) or quaternary ammonium (Q). Additionally, AGP can be contacted with a cation exchange resin under conditions in which impurities are bound to the resin and AGP is recovered in the effluent. The functional group of the cation exchange resin can be carboxymethyl (CM) or sulphonyl, such as sulphopropyl (SP). Other chromatographic methods can also be applied, such as hydrophobic interaction chromatography, chelate affinity chromatography and adsorption chromatography.

A therapeutic preparation of AGP and AAT must be safe with respect to potential blood-borne viruses, which can be accomplished by having at least one virus inactivation or removal step in the manufacturing process, which is effective against both enveloped and nonenveloped viruses, and by limiting the potential virus load in the starting plasma by sensitive virus screening tests. The therapeutic preparations should have a low endotoxin level (<0.1 IU/mg protein by the LAL test). The purity of plasma-derived AGP and AAT in the therapeutic preparation should be at least 80% as studied by cellulose acetate or agarose gel electrophoresis before possible addition of albumin or other stabilizer proteins. The purity of transgenic or recombinant AGP and AAT should be at least 99%.

AGP can be subjected to virus inactivation by several methods, such as solvent detergent (SD) method and pasteurization for 10 h at 60° C. SD treatments are disclosed in the art, in particular in U.S. Pat. Nos. 4,540,573, 4,764,369 and 4,820,805, the contents of which are herewith incorporated by reference. The organic solvent is preferably selected from dialkylphosphates and trialkylphosphates having alkyl groups which contain 1 to 10 carbon atoms. Examples of trialkylphosphates are tri-(n-butyl)-phosphate, tri-(t-butyl) phosphate, tri-(n-hexyl)phosphate and tri-(2-ethylhexyl)-phosphate. The concentration of the solvent is in the range of 0.01 g/l to 100 g/l, preferably about 0.1 g/l to about 10 g/l, a typical concentration of tri-(n-butyl)phosphate being about 0.3%. The solvent can be used together with a non-toxic detergent, which is capable of enhancing the effectiveness of the solvent. The SD chemicals can be removed from AGP for example by binding AGP to an anion exchange resin, removing SD substances by washing the resin and eluting the AGP from the resin.

Another method for the elimination of possible blood borne viruses from AGP is virus filtration. As AGP has a relatively small molecular weight (about 41 kD), it can be readily filtered with virus removal filters with very small pore size, such as 15 nm, which effectively remove even smallest non-enveloped viruses. Successful filtration with 15 nm virus removal filters has been before described for plasma proteins, such factor IX and factor XI with molecular sizes of 55 kD and 143 kD, respectively (Burnouf-Radosevich M. et al., Vox Sang. 67, 132–138, 1994).

In one purification method of AGP (Hao Y. -L. and Wickerhauser M., Biophys. Biochim. Acta 322:99–108, 1973), Fraction V supernatant (pH 4.7) is stirred with DEAE-Sephadex A-50 gel equilibrated with 25 mM sodium acetate buffer pH 4.1 for 90 min at 0 to 10° C. After washing the gel with the cold acetate buffer the adsorbed fraction is eluted with the acetate buffer containing 1 M NaCl. The eluate is concentrated and diafiltered with the acetate buffer by ultrafiltration. The diafiltered concentrate is then applied to a column of CM-gel equilibrated with the acetate buffer and AGP is recovered in the column effluent. The pure AGP preparation is concentrated and diafiltered against water for injection (WFI) or 150 mM sodium chloride by ultrafiltration. The solution is neutralized with 0.5 M NaOH and filtered through a virus filter with pore size of 15 nm. The solution is sterile filtered, and filled aseptically into sterile containers. The product can be lyophilized.

In another purification method, disclosed in more detail in published patent application WO97/32893, Fraction V supernatant is applied to a column of Q Sepharose Big Bead equilibrated with 0.13 M sodium acetate buffer pH 4.1 at 10° C. The column is washed with about 5 bed volumes of the acetate buffer and AGP eluted with the acetate buffer containing 0.2 M sodium chloride. The AGP preparation is neutralized and treated for 2 hours at 20° C. with Aerosil (1 g Aerosil per 1 g AGP) to remove possible pyrogens. The AGP preparation is concentrated by ultrafiltration and diafiltered against 10 mM sodium phosphate, 150 mM NaCl, pH 7.5. The solution is filtered through a virus filter with pore size of 15 nm, sterile filtered and filled aseptically into sterile containers. The product is pasteurized in the final containers for 10 hours at 60° C.

By both described methods, virus-safe and pure AGP having a low pyrogen content and being suitable for intravascular administration to humans is obtained.

In summary, according to a preferred embodiment of the present invention, AGP is purified from Cohn fraction V supernatant of human plasma by a method comprising anion exchange chromatography, ultrafiltration, virus filtration and at least one virus inactivation step consisting of solvent detergent treatment or pasteurization.

AAT may be purified from human plasma starting for example from Cohn fraction IV precipitate by different described methods (cf. for example U.S. Pat. No. 5,610,285, the contents of which is herewith incorporated by reference).

As apparent to a person skilled in the art, therapeutic compositions of AGP and AAT may contain various known excipients and stabilizers. They may also be combined with each other or given at the same time as separate compositions. Further, they can be combined either in the same composition or as different compositions with other active substances in the treatment of clinical conditions associated with I/R injury.

Typically, therapeutically useful pharmaceutical compositions—preferably formulated for parenteral use—contain AGP or AAT or mixtures thereof in concentrations of 1–200 g/l, preferably about 10 to 100 g/l. Pharmaceutical compositions of AGP and AAT may also comprise freeze-dried powder, which can be reconstituted to a suitable volume before administration to a patient or addition to a preservation solution of organs or tissues.

The following non-limiting examples illustrate the invention:

EXAMPLE 1

AGP and AAT Reduce Early and Delayed Reperfusion-Induced Apoptosis After Ischemia To induce renal I/R, mice weighing 20–25 g were subjected to 45 minutes of unilateral ischemia of the left kidney by clamping the renal vessels as described before (Daemen M. A. et al., Circulation 102:1420–1426, 2000). Contralateral nephrectomy was performed and the clamp removed, At reperfusion, 12 mice were administered intraperitoneally 5 mg bovine or human AGP or 0.5 mg human AAT in 0.5 ml sterile PBS, which resulted in serum concentrations similar to those observed during acute phase reaction. 8 mice received AGP or AAT 2 hours after reperfusion. 10 control mice received 0.5 ml PBS and 12 sham-operated mice were subjected to same procedure without clamping the renal vessels and treated with PBS. The animals were euthanized at indicated time points and blood samples were collected and the left kidney harvested. The same model of I/R injury was used in all examples.

Figure 1:
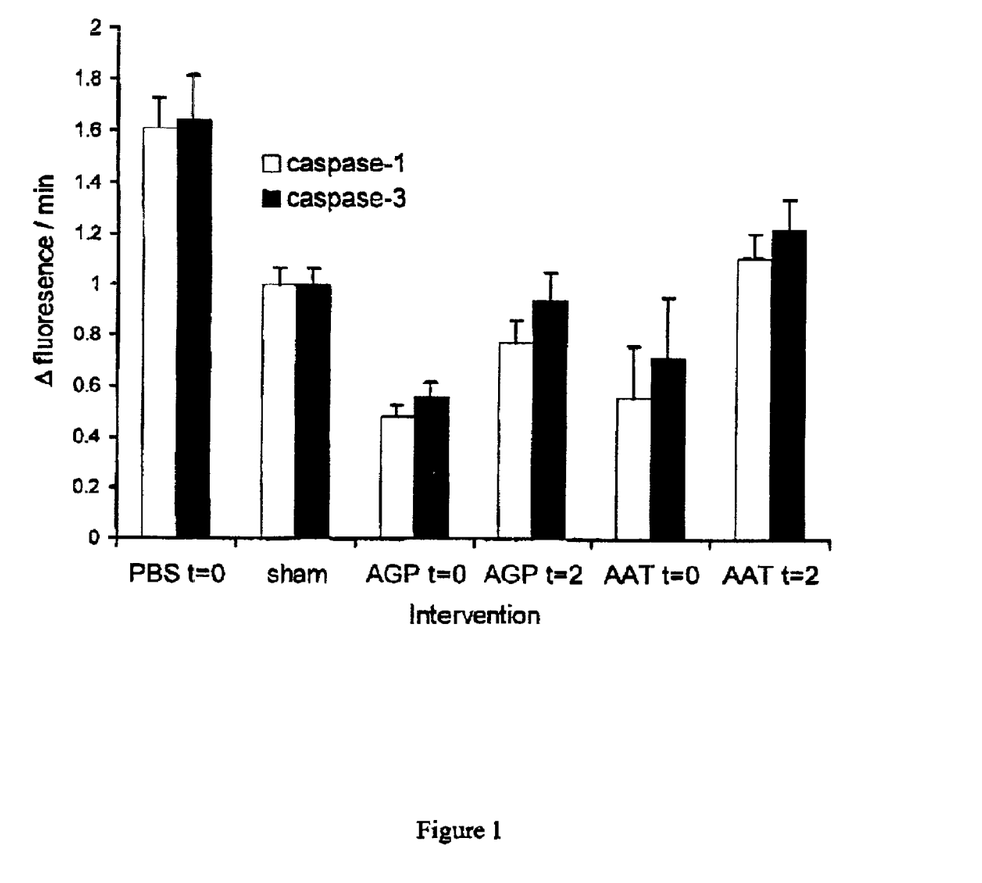
FIG. 1 shows the prevention of reperfusion-induced apoptotic cell death in ischemic kidney by AGP and AAT administration. Apoptosis was assessed by measuring caspase-1 and caspase-3 activities in kidney homogenates 24 hours after reperfusion. The mice were given the treatments indicated at the time point of reperfusion (t=0) or two hours after it (t=2). Data present mean±SEM, *P<0.05 vs. PBS-treated control animals.

Development of reperfusion-induced apoptotic cell death in the kidney was assessed by determination of intranucleosomal DNA cleavage, caspase-1 and caspase-3 activities and TUNEL microscopy as described before (Daemen M. A. et al., Circulation 102:1420–1426, 2000). No internucleosomal DNA cleavage was detected at 2 hours of reperfusion in kidneys obtained from mice treated with either AGP or AAT, whereas clear DNA cleavage was observed in PBS-treated mice. These early effects of AGP and AAT indicated direct inhibition of apoptosis as early primary apoptosis precedes the first signs of inflammation during I/R injury. As indicated by the absence of apparent internucleosomal DNA cleavage, decreased numbers of TUNEL-positive nuclei, and attenuated caspase-1 and caspase-3 activities (FIG. 1), Apoptosis was also effectively reduced after 24 hours in mice treated with either AGP or AAT compared with PBS-treated control mice.

The therapeutic effect was less when AGP and AAT were administered 2 hours after reperfusion. Compared with PBS treatment, AAT administered at 2 hours of reperfusion decreased caspase-1- and caspase-3-like activities after 24 hours of reperfusion (FIG. 1), but did not reduce internucleosomal DNA cleavage. AGP reduced caspase-1 and caspase-3-like activities (FIG. 1) and prevented internucleosomal DNA cleavage after 24 hours.

Dose response of the therapeutic effect of AGP was studied by determining internucleosomal DNA cleavage 2 hours after reperfusion and administration of different doses of AGP. A single dose of 1.7 mg AGP at reperfusion sufficed to effectively reduce internucleosomal DNA cleavage. The therapeutic effect gradually declined when doses of 0.5 or 0.17 mg AGP were used.

EXAMPLE 2

AGP and AAT Reduce Reperfusion-Induced Inflammation After Ischemia

Figure 2:
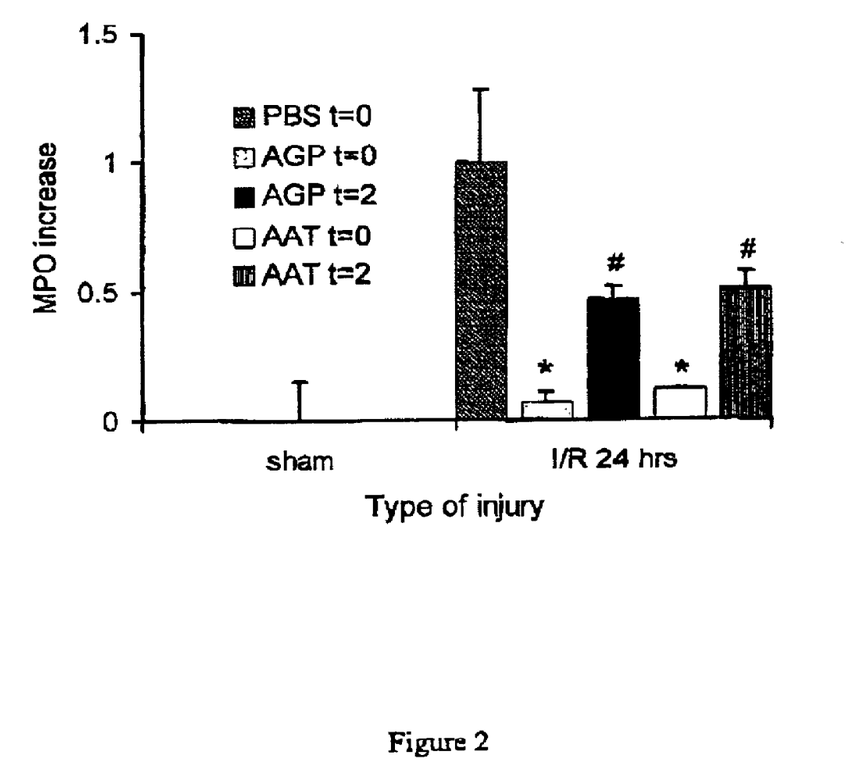
FIG. 2 shows the inhibition of reperfusion-induced inflammatory reaction in ischemic kidney by AGP and AAT administration. Inflammatory reaction was assessed by myeloperoxidase (MPO) determination 24 hours after reperfusion, which indicates neutrophilic influx to the renal tissue. The mice were given the treatments indicated at the time point of reperfusion (t=0) or two hours after it (t=2).

The effects of AGP and AAT on reperfusion-induced inflammation were studied by assessing renal TNF-α expression and neutrophil influx. AGP and AAT administered at time of reperfusion effectively limited TNF-α expression and neutrophil influx, studied at 24 hours after initiation of reperfusion (FIG. 2). AGP and AAT given after 2 hours of reperfusion attenuated the inflammation at 24 hours to a lesser extent than did treatment given at time of reperfusion (FIG. 2). However, treatments at both time points decreased inflammation compared with PBS treatment when assessed 24 hours after reperfusion (FIG. 2). The PBS-treated control mice showed significant renal inflammation as reflected by TNF-α expression in the outer stripe of the outer medulla, along the damaged tubular epithelium, and in infiltrating leukocytes. Also, significant renal neutrophil accumulation was reflected by an enhanced myeloperoxidase (MPO) content (FIG. 2) and accumulation of anti-neutrophil antibody-positive cells.

EXAMPLE 3

AGP and AAT Prevent Reperfusion-Induced Renal Dysfunction After Ischemia

Figure 3:
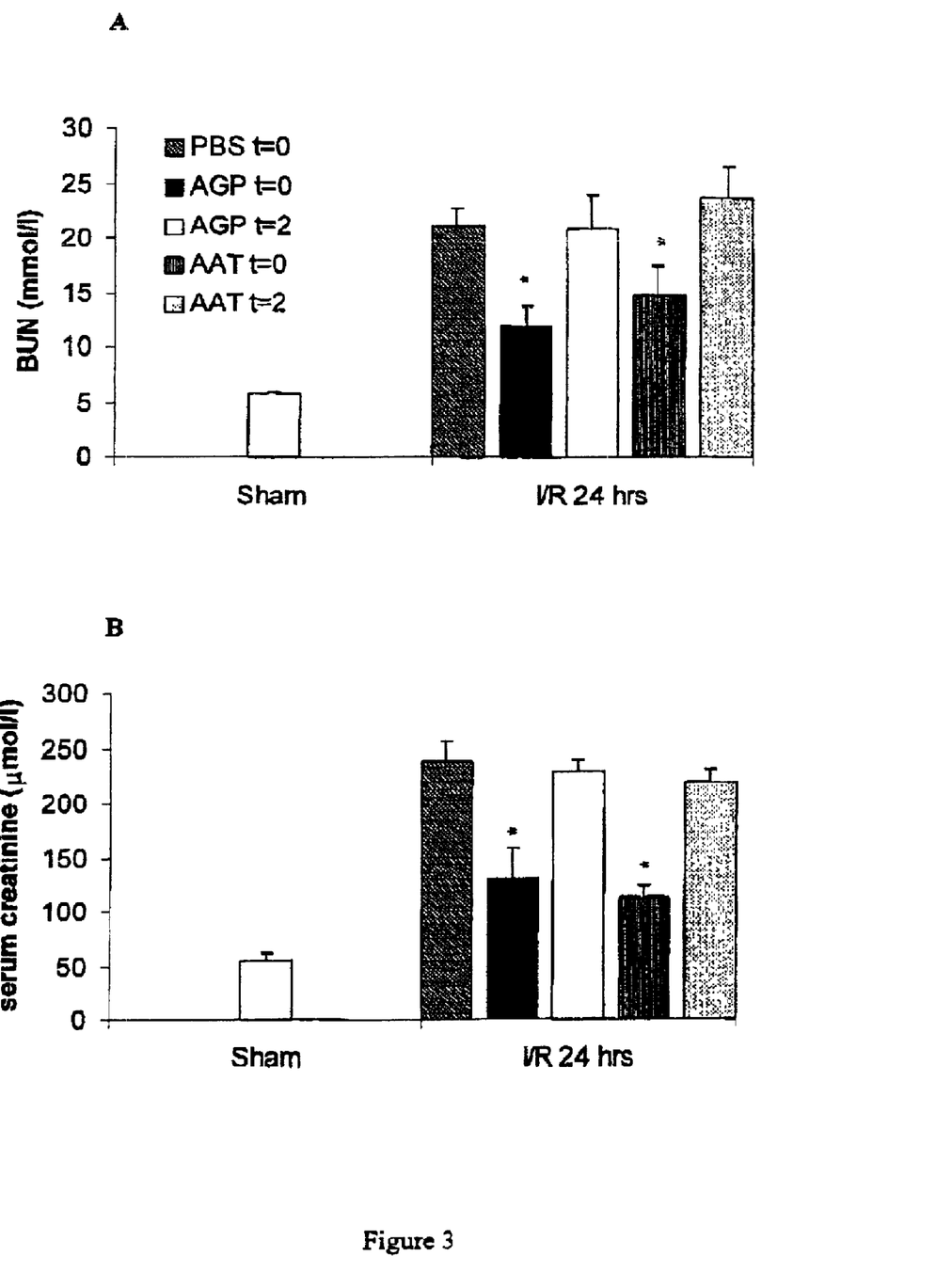
FIGS. 3A–B show the prevention of reperfusion-induced renal dysfunction after ischemia by AGP and AAT administration. Renal function was assessed by the blood urea nitrogen (BUN) (A) and serum creatinine determinations (B) 24 hours after reperfusion of the ischemic kidney. The mice were given the treatments indicated at the time point of reperfusion (t=0) or two hours after it (t=2).
Figure 4:
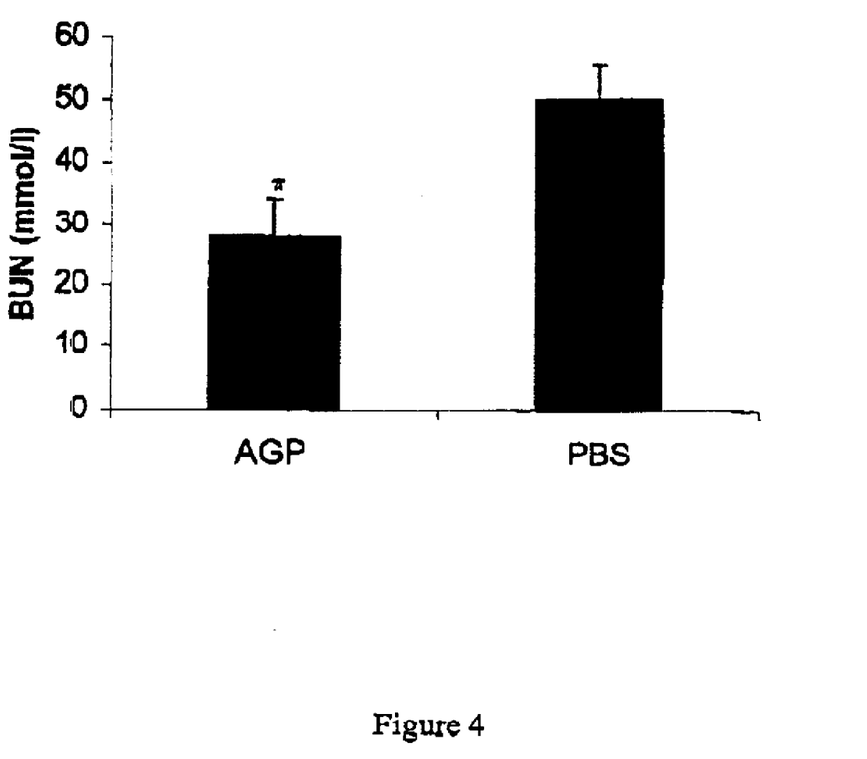
FIG. 4 shows the prevention of reperfusion-induced impairment of renal function after ischemia by human plasma AGP. AGP and PBS (phosphate buffered saline) were administered to the mice at the time point of reperfusion of the ischemic kidney and renal function was assessed by the blood urea nitrogen (BUN) determination.

Ischemia-reperfusion of the kidneys resulted in renal dysfunction as reflected by increased blood urea nitrogen (BUN) content and serum creatinine levels 24 hours after reperfusion (FIGS. 3A and B). Compared with PBS, both AGP and AAT administered at time of reperfusion effectively lowered BUN content and serum creatinine levels. However, when administered 2 hours after reperfusion, AGP and AAT failed to significantly decrease BUN or serum creatinine compared with PBS (FIGS. 3A and B). These findings illustrate the importance of the prevention of early apoptotis after reperfusion and the necessity to administer AGP and AAT at the time point of reperfusion in order to achieve optimal therapeutic effect in the prevention of I/R injury. Bovine AGP (FIG. 3), human plasma AGP (FIG. 3) and human AGP lacking the sLe$^x$ carbohydrate structure had similar efficacy in preventing reperfusion-induced renal dysfunction after ischemia.

EXAMPLE 4

Preparation of AGP from Human Plasma 980 kg of Fraction V supernatant was obtained from 1500 kg of human plasma during purification of albumin by Cohn fractionation. The supernatant was filtered through a Cuno Zeta Plus depth filter and stirred for 3 h at 4° C. with 80 l of pre-swelled DEAE-Sephadex A-50 gel equilibrated with 25 mM sodium acetate buffer, pH 4.1. The gel was allowed to sediment, the supernatant siphoned away and the gel was washed 5 times with 40 l of the acetate buffer. AGP was eluted from the gel with 160 l of the acetate buffer containing 1 M NaCl. The eluate was concentrated to 3000 ml using 30 kD cut-off ultrafiltration membranes and diafiltered against 25 mM sodium acetate buffer, pH 4.1. The AGP solution was applied to a column of CM-Trisacryl M (bed volume 1.3 l) equilibrated and eluted with the 25 mM sodium acetate buffer, pH 4.1. AGP was recovered in the column effluent, concentrated to a protein concentration of 70 g/l by ultrafiltration and diafiltered against WFI. The pH was neutralized and the solution was filtered through a Planova 15N virus filter. The solution was sterile filtered, filled aseptically into sterile containers and lyophilized. Before administration, he product Was reconstituted with sterile 150 mM NaCl to a protein concentration of 10 g/l.

The purity of AGP in the product was more than 95% according to cellulose acetate electrophoresis. 97.5% of the protein was monomeric AGP, 2.5% corresponded to dimers, and no polymers or aggregates were detected by size exclusion HPLC. The endotoxin level was 0.02 IU/mg according the LAL-test (Ph. Eur. 3rd Ed. S. 2.6.14.A, 2000) and the product was free of pyrogens when tested at a dose of 100 mg/kg in rabbits.

A fraction of human plasma AGP containing sLe$^x$ determinants was removed by affinity chromatography using agarose-bound *Aleuria aurantia* lectin (De Graaf T. W. et al., J. Exp. Med. 177:657–666, 1993) according to the manufacturer's instructions (Vector Laboratories). AGP lacking the sLe$^x$ determinant was recovered in the effluent and the lectin-bound fraction was eluted with 100 mM fucose. About 10% of human plasma AGP bound to the column.

What is claimed is:

1. A method of protecting organs or tissue susceptible to reperfusion-induced dysfunction after ischemia, comprising contacting said organs or tissue with an increased concentration of natural alpha-1 acid glycoprotein, natural alpha-1 antitrypsin or a mixture thereof, relative to the base levels of the natural alpha-1 acid glycoprotein and the natural alpha-1 antitrypsin in the organs or tissue.

2. The method according to claim 1, wherein said organs or tissue are contacted with natural alpha-1 acid glycoprotein, natural alpha-1 antitrypsin or mixtures thereof by parenterally administering to a patient, who has organs or tissue susceptible to a condition of reperfusion-induced dysfunction after ischemia, a therapeutical composition containing natural alpha-1 acid glycoprotein, natural alpha-1 antitrypsin or a mixture thereof.

3. The method according to claim 2, wherein natural alpha-1 acid glycoprotein, natural alpha-1 antitrypsin or mixtures thereof are parenterally administered to a patient in a concentration sufficient to raise plasma concentration of said proteins to a level corresponding to the levels of the natural alpha-1 acid glycoprotein and the natural alpha-1 antitrypsin that occur in plasma during inflammatory conditions.

4. The method according to claim 2 or claim 3, wherein natural alpha-1 acid glycoprotein is administered in a concentration sufficient to raise plasma concentration of said natural alpha-1 glycoprotein to a level of 0.2 to 5 g/l.

5. The method according to claim 4, wherein natural alpha-1 acid glycoprotein or natural alpha-1 antitrypsin, each individually, or a mixture of alpha-1 acid glycoprotein and alpha-1 antitrypsin is administered in an intravascular dose of 20 to 500 mg/kg/day.

6. The method according to claim 2, wherein said therapeutic composition containing natural alpha-1 acid glycoprotein, natural alpha-1 antitrypsin or a mixture thereof is parenterally administering to the recipient of an organ transplant.

7. The method according to claim 6, wherein said therapeutic composition is administered to the recipient patient not later than at the immediate initiation of the reperfusion period.

8. The method according to claim 6 or 7, wherein said therapeutic composition is intravenously administered to the recipient patient during the transplantation.

9. The method according to claim 1, wherein said organs or tissue comprise organ or tissue transplants which are contacted with natural alpha-1 acid glycoprotein, natural alpha-1 antitrypsin or mixtures thereof by perfusing or flushing them with a solution containing natural alpha-1 acid glycoprotein, natural alpha-1 antitrypsin or mixtures thereof in a concentration of 0.1 to 5 g/l.

10. The method according to claim 9, wherein said organs or tissue are perfused with a solution containing, in addition to natural alpha-1 acid glycoprotein, natural alpha-1 antitrypsin or a mixture thereof, at least one component selected from the group consisting of electrolytes and cell-protecting agents.

11. The method according to claim 1, wherein the natural alpha-1 acid glycoprotein or natural alpha-1 antitrypsin comprises human plasma-derived alpha-1 acid glycoprotein or alpha-1 antitrypsin having a purity of at least 80% or transgenic or recombinant alpha-1 acid glycoprotein or alpha-1 antitrypsin having an amino acid sequence essentially identical with that of the corresponding human alpha-1 acid glycoprotein or human alpha-1 antitrypsin and having a purity of at least 99%.

12. The method according to claim 11, wherein the natural alpha-1 acid glycoprotein or natural alpha-1 antitrypsin comprises a virus-safe therapeutic composition having an endotoxin level of less than 0.1 IU/mg protein as measured by the limulus amebocyte lysates (LAL) test.

13. A method of protecting organ or tissue transplants against reperfusion injury and dysfunction, comprising contacting said organ or tissue with a preservation fluid for perfusion and storage or rinsing of the organ, or tissue transplants prior to the implantation of said organ or tissue in a patient requiring such implantation, wherein said preservation fluid contains natural alpha-1 acid glycoprotein, natural alpha-1 antitrypsin or a mixture thereof in a concentration sufficient to prevent reperfusion-induced organ dysfunction after ischemia.

14. The method according to claim 13, wherein natural alpha-1 acid glycoprotein, natural alpha-1 antitrypsin or a mixture thereof is added in a concentration of 0.1 to 5 g/l of preservation or rinse fluid.

15. The method according to claim 13 or claim 14, wherein the natural alpha-1 acid glycoprotein or natural alpha-1 antitrypsin comprises mammal plasma-derived alpha-1 acid glycoprotein or alpha-1 antitrypsin having a purity of at least 80% or transgenic or recombinant alpha-1 acid glycoprotein or alpha-1 antitrypsin having an amino acid sequence identical with that of the corresponding human alpha-1 acid glycoprotein or human alpha-1 antitrypsin and having a purity of at least 99%.

16. The method according to claim 15, wherein the natural alpha-1 acid glycoprotein or natural alpha-1 antitrypsin comprises a virus-safe therapeutical composition having an endotoxin level of less than 0.1 IU/mg protein as measured by the limulus amebocyte lysates (LAL) test.

17. A method of protecting organ and tissue transplants against reperfusion injury and dysfunction, comprising administering human alpha-1 acid glycoprotein or human alpha-1 antitrypsin, individually or in combination to the recipient of an organ or tissue transplant.

18. A method of protecting organs against reperfusion injury and dysfunction comprising administering an effective amount of human alpha-1 acid glycoprotein or human alpha-1 antitrypsin, individually or in combination to a patient undergoing surgical operation.

19. A method of protecting an organ against reperfusion injury and dysfunction comprising administering an effective amount of human alpha-1 acid glycoprotein or human alpha-1 antitrypsin, individually or in combination to a patient undergoing thrombolytic therapy or revascularisation procedures.

20. A method of protecting organs against reperfusion injury and dysfunction comprising administering an effective amount of human alpha-1 acid glycoprotein or human alpha-1 antitrypsin, individually or in combination to a patient during treatment of bleeding shock or other forms of shock and hypoperfusion of organs.

21. The method according to any one of claims 17 to 20, wherein alpha-1 acid glycoprotein is administered intravascularly at a dose of 20–500 mg/kg/day.

22. The method according to any one of claims 17 to 20, wherein alpha-1 antitrypsin is administered intravascularly at a dose of 20–500 mg/kg/day.

23. The method according to anyone of claims 1, 9 and 17 to 20, wherein the human alpha-1 acid glycoprotein has been purified from Cohn fraction V supernatant of human plasma by a method comprising anion exchange chromatography, ultrafiltration, virus filtration and at least one virus inactivation step consisting of solvent detergent treatment or pasteurization.

* * * * *